United States Patent [19]
McKinnon et al.

[11] Patent Number: 5,503,627
[45] Date of Patent: * Apr. 2, 1996

[54] AMPULE FOR NEEDLELESS INJECTION

[75] Inventors: Charles M. McKinnon, Laguna Niguel, Calif.; Takaaki Nakagawa, Tigard; Carl E. Wilcox, Portland, both of Oreg.

[73] Assignee: Bioject, Inc., Portland, Oreg.

[*] Notice: The portion of the term of this patent subsequent to May 17, 2011, has been disclaimed.

[21] Appl. No.: 239,884

[22] Filed: May 9, 1994

Related U.S. Application Data

[63] Continuation of Ser. No. 714,892, Jun. 13, 1991, Pat. No. 5,312,335, which is a continuation-in-part of Ser. No. 547,898, Jul. 2, 1990, abandoned, which is a continuation-in-part of Ser. No. 434,250, Nov. 9, 1989, Pat. No. 5,064,413.

[51] Int. Cl.$^6$ ..................................................... A61M 5/30
[52] U.S. Cl. .................................. 604/72; 604/68
[58] Field of Search ....................... 604/68–72, 240–243; 206/365

[56] References Cited

U.S. PATENT DOCUMENTS

| | | |
|---|---|---|
| 1,742,497 | 1/1930 | Dickinson ............................ 604/242 |
| 2,025,219 | 12/1935 | Smith . |
| 2,322,245 | 6/1943 | Lockhart . |
| 2,670,121 | 2/1954 | Scherer et al. . |
| 2,688,968 | 9/1954 | Scherer . |
| 2,704,543 | 3/1955 | Scherer . |
| 2,714,887 | 8/1955 | Venditty . |
| 2,737,946 | 3/1956 | Hein, Jr. . |
| 2,816,543 | 12/1957 | Venditty et al. . |
| 2,821,193 | 1/1958 | Ziherl et al. . |
| 2,902,995 | 9/1959 | Loper . |
| 3,179,107 | 4/1965 | Clark . |
| 3,490,451 | 1/1970 | Yahner . |
| 3,557,784 | 1/1971 | Shields . |
| 3,688,765 | 9/1972 | Gasaway . |
| 3,714,943 | 2/1973 | Yanof et al. . |
| 3,802,430 | 4/1974 | Schwebel et al. . |
| 3,853,125 | 12/1974 | Clark . |
| 3,945,379 | 3/1976 | Pritz et al. . |
| 3,945,383 | 3/1976 | Bennett et al. . |
| 4,124,024 | 11/1978 | Schwebel et al. . |
| 4,240,428 | 12/1980 | Akhavi . |
| 4,507,113 | 3/1985 | Dunlap . |
| 4,596,556 | 6/1986 | Morrow et al. . |
| 4,623,332 | 11/1986 | Lindmayer et al. . |
| 4,680,027 | 7/1987 | Parsons et al. . |
| 4,790,824 | 12/1988 | Morrow et al. . |
| 4,874,367 | 10/1989 | Edwards . |
| 4,940,460 | 7/1990 | Casey . |
| 4,941,880 | 7/1990 | Burns . |
| 4,966,581 | 10/1990 | Landau . |
| 5,062,830 | 11/1991 | Dunlap . |
| 5,080,648 | 1/1992 | D'Antonio . |
| 5,312,335 | 5/1994 | Mekinnon et al. ................. 604/72 |

FOREIGN PATENT DOCUMENTS

| | | |
|---|---|---|
| 2627698 | 2/1988 | France . |
| 138338 | 1/1961 | U.S.S.R. . |
| 1047562 | 11/1966 | United Kingdom . |
| 9015633 | 12/1990 | WIPO . |

Primary Examiner—Stephen C. Pellegrino
Assistant Examiner—Nancy Mulcare
Attorney, Agent, or Firm—Lyon & Lyon

[57] ABSTRACT

A needleless injection device has a housing containing a pilot valve connectable to a compressed gas source. A two stage power amplifying valve includes a main valve operatively connected to the pilot valve. The pilot valve and main valve form a two-stage valve with the pilot valve activatable to open the main valve utilizing gas pressure. Compressed gas in a reservoir flows through the open main valve to drive a plunger into an ampule to inject an injectant through a patient's skin. Interlocks are provided to resist inadvertent actuation of the device and a indicator indicates whether there is sufficient gas pressure in the device for another injection.

18 Claims, 14 Drawing Sheets

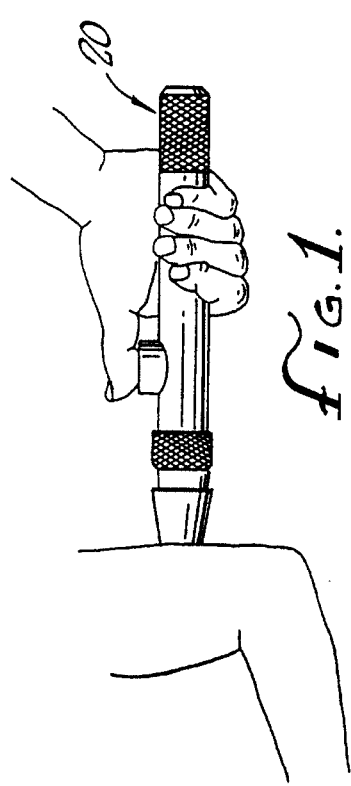
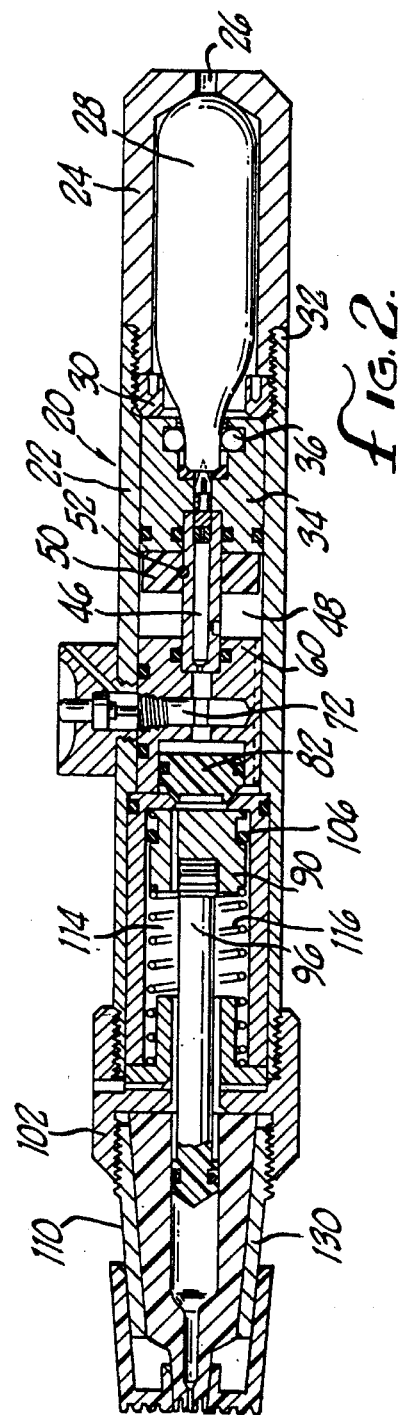
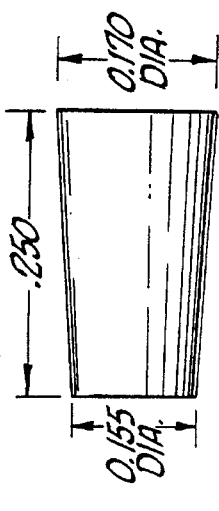

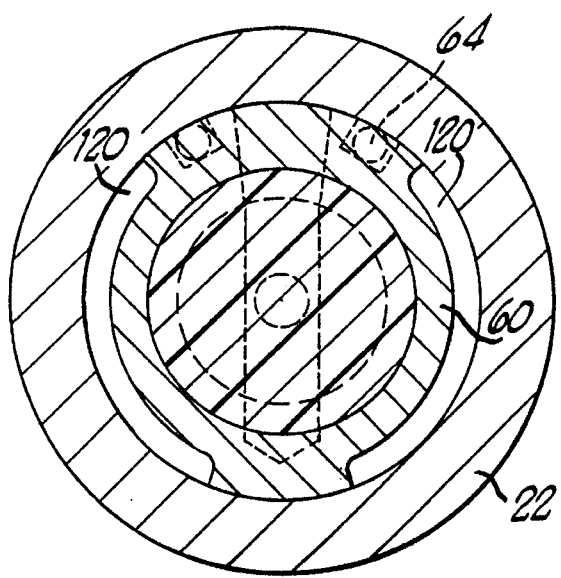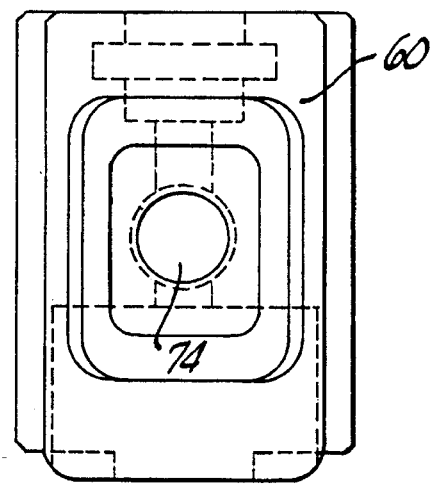

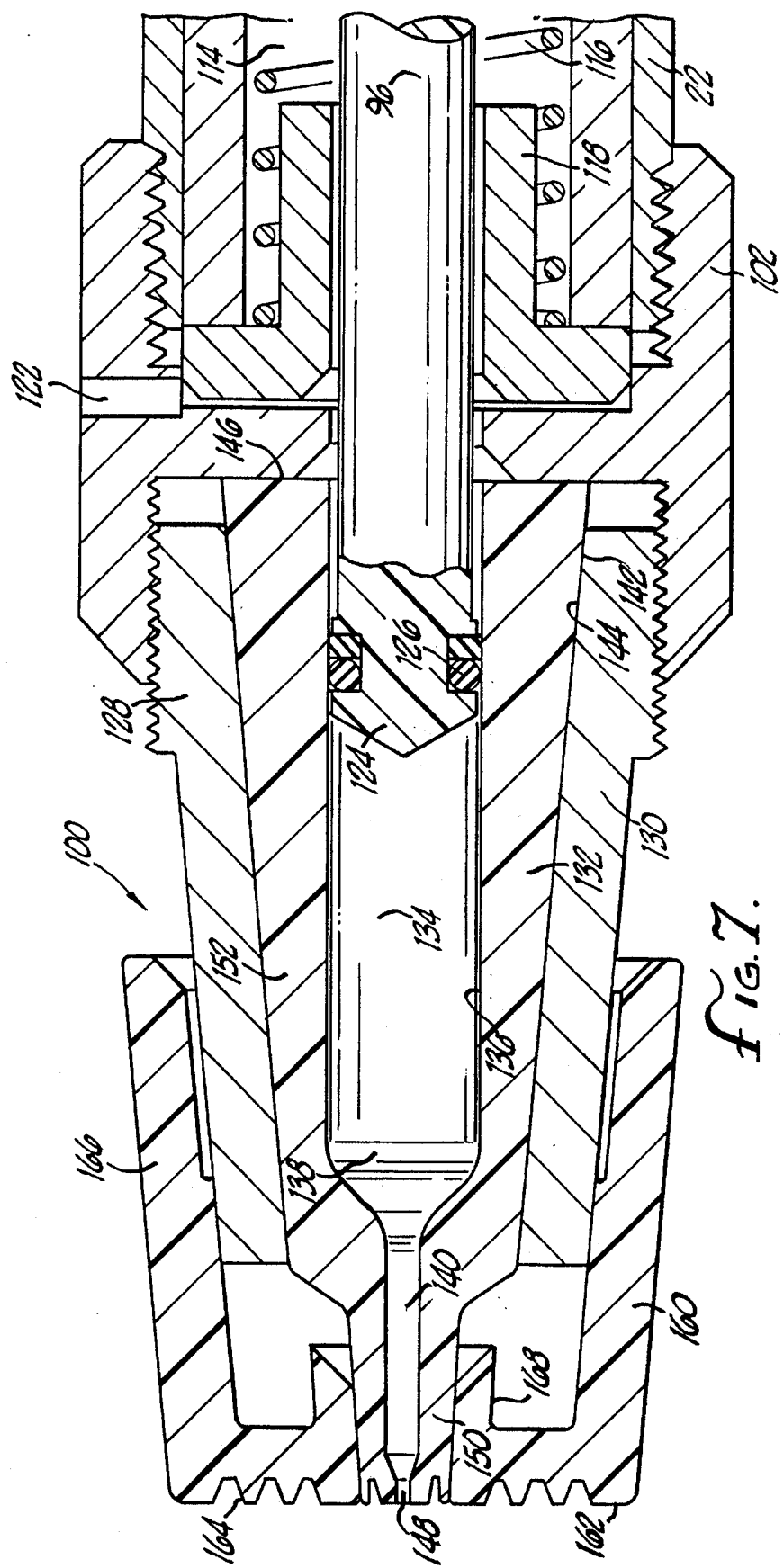

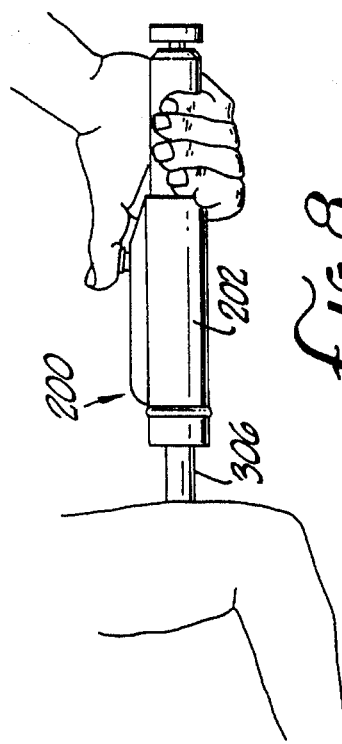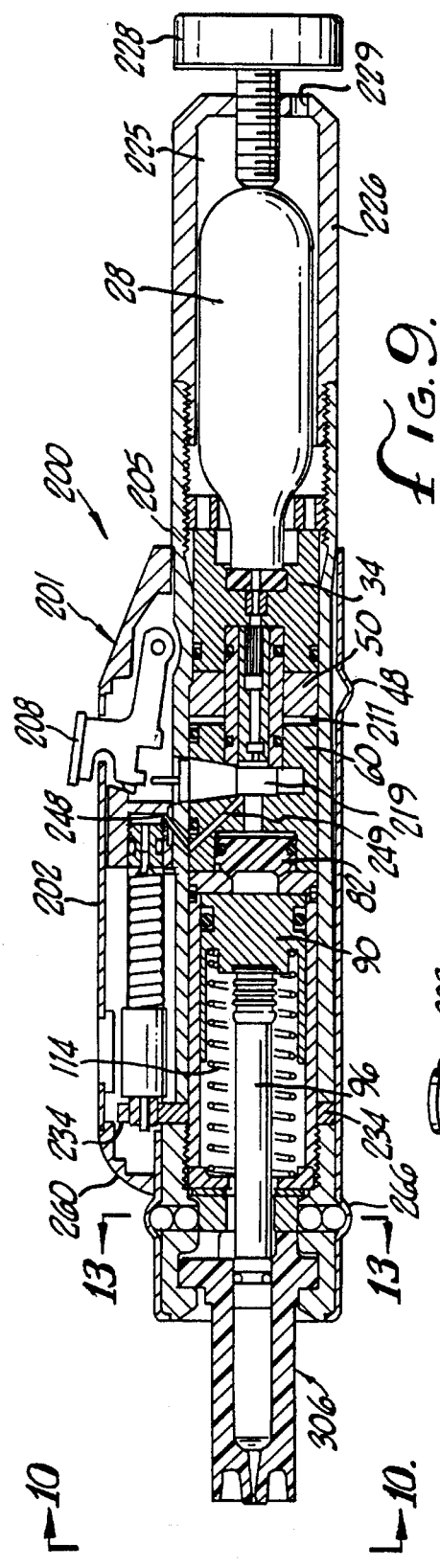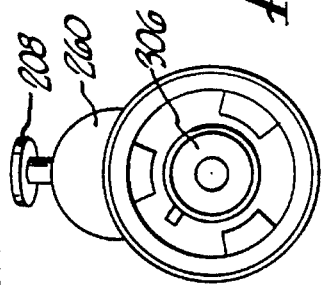

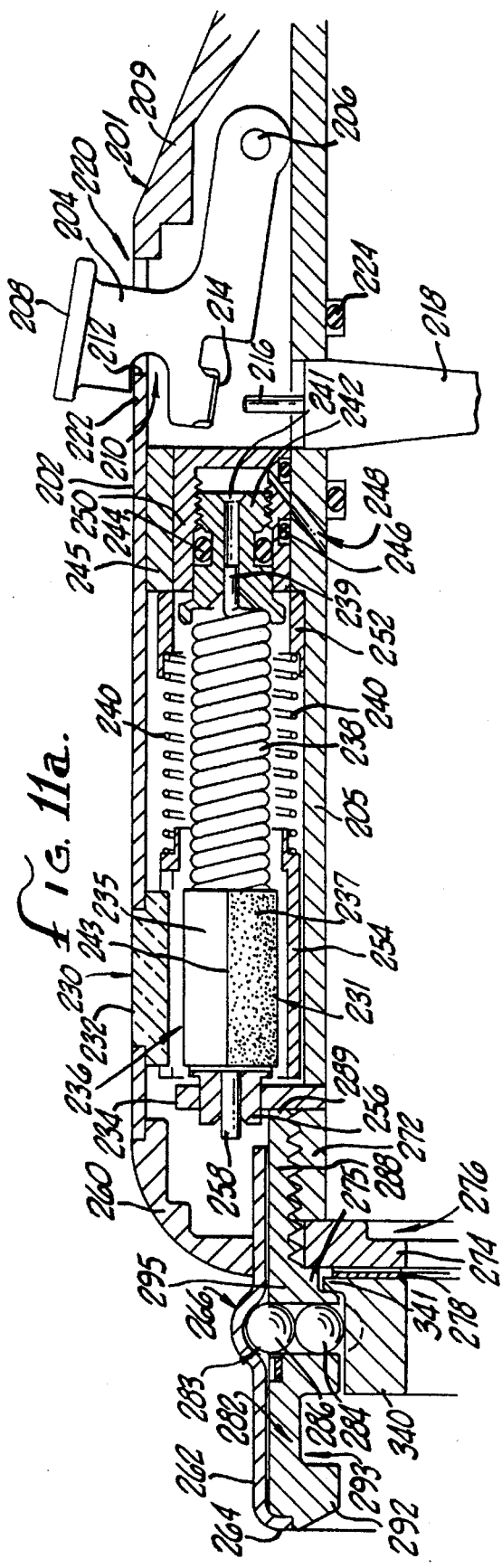

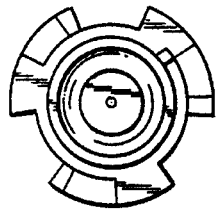
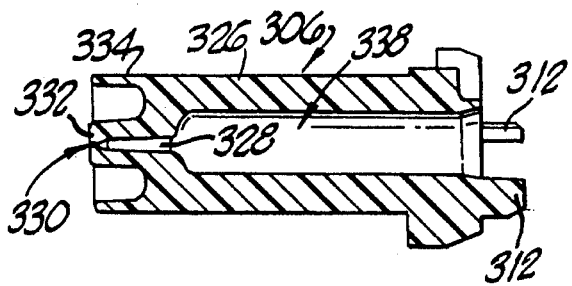
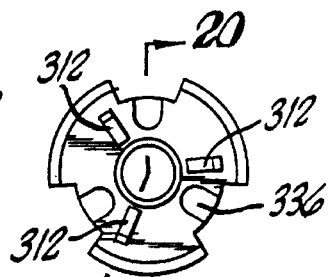
fig.18.  fig.20.  fig.19.
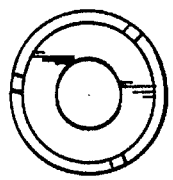
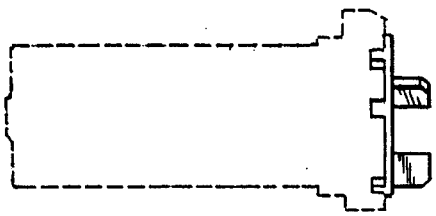
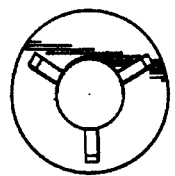
fig.21.  fig.23.  fig.22.
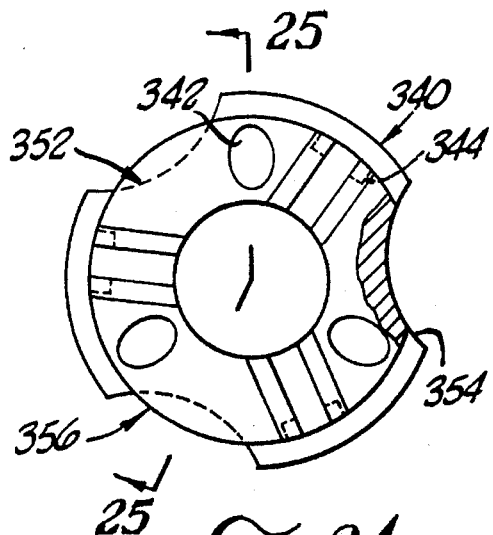
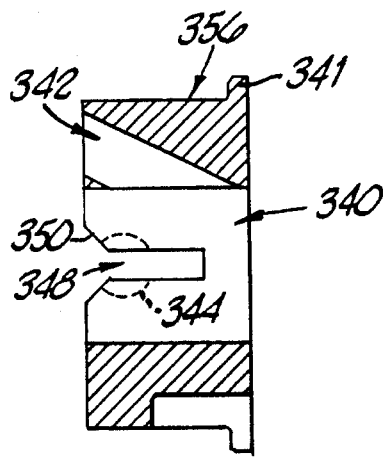
fig.24.  fig.25.

TANGENT POINT 5,503,627

AMPULE FOR NEEDLELESS INJECTION

This is a continuation of U.S. patent application Ser. No. 07/714,892, now U.S. Pat. No. 5,312,335, which is a continuation-in-part of U.S. patent application Ser. No. 07/547,898 filed Jul. 2, 1990 and now abandoned, which is a continuation-in-part of U.S. patent application Ser. No. 07/434,250 filed Nov. 9, 1989 and now U.S. Pat. No. 5,064,413.

BACKGROUND OF THE INVENTION

The field of the present invention is needleless hypodermic injection devices. More particularly, the invention relates to needleless hypodermic devices utilizing pressurized gas for injection of medication.

Various needleless hypodermic injection devices have been known in the past. For example, Morrow et al, U.S. Pat. No. 4,790,824 describes a needleless hypodermic injection device having a two-stage gas delivery system and an ampule shroud containing medication which is driven through the skin via gas pressure.

Parsons et al, U.S. Pat. No. 4,680,027 discloses an injection device using a pressurized gas cartridge to drive a piston against the biasing force of a spring. The driven piston works on a syringe causing liquid medication to be ejected with sufficient pressure to penetrate the skin of the patient.

While these and other known injection devices have met with varying degrees of success, their constructions or operating features can prevent effective injection. It has now been discovered that the injection of liquid medication or injectant should be as instantaneous as possible. With gas powered injection devices, the rise time of the gas pressure acting on the piston, and the resulting acceleration at which the piston and injectant are driven is critical. When the gas pressure acting on the piston rises too slowly, the initial medication ejected from the device does not have sufficient pressure or velocity to pass through the skin. In addition, if the "rise time" of the injection sequence is not sufficiently fast, a substantial portion of the medication will be too slowly driven from the device causing a "splash back" condition. Consequently, as a result of "splash back" the patient does not receive the full dosage of medication.

In gas driven injection devices, there are several factors which may effect the efficiency of the device. For example, devices having a long or tortuous gas path will have slower rise times due to flow losses and gas volume compressibility effects. In addition, certain injection devices rely on direct mechanical valve operation by the user of the device to release the gas pressure during the injection sequence. Since the valve operation is done manually in these devices, the effectiveness of the injection can vary widely with the user, due to the speed, activating force and completeness of activating movement employed by different users of the device. More importantly, it has not been previously appreciated that many of these types of devices have relatively large "dead" spaces or volumes of gas trapped behind the piston when the device in the ready to fire condition. These dead volumes substantially hinder injection by slowing the rise time of the gas pressure acting on the piston since substantial time is required for relatively large volumes of gas to flow into the dead volumes to build up an adequate injection pressure.

Gas driven injection devices can also be inadvertently activated if the valve of the device is inadvertently depressed or opened by the user, or if the user should drop the device, etc. This results in wasted injected medication and driving compressed gas.

Gas driven injection devices using compressed gas cartridges can provide a limited number of injections before the cartridge must be replaced with a fresh cartridge. With each injection, some compressed gas is expended thereby decreasing the available supply of compressed gas remaining in the device. After a certain number of injections, the available compressed gas pressure within the device becomes inadequate for proper injection. Consequently, depending on the type of device and the type of injections being provided by the device, it has been necessary for the user of the device to keep track of the number of injections provided by the cartridge in the device, and to replace the cartridge after a maximum specified number of injections. If the maximum number of injections per cartridge is exceeded, the decreased and insufficient gas pressure available can lead to "splash back" as described above.

Accordingly, it is an object of the invention to provide an improved needleless hypodermic injection device.

It is another object of the invention to provide a novel ampule assembly which may be advantageously used with such a needleless injection device.

It is another object of the invention to provide a novel method of subcutaneous or intramuscular injection.

It is yet another object of the invention to provide such a needleless injection device having an interlock to help prevent inadvertent actuation of the device.

It is still another object of the invention to provide such an injection device having a gas pressure indicator to indicate whether the device has sufficient gas pressure for the next injection.

SUMMARY OF THE INVENTION

These and other related objects are achieved according to the invention by an injection device having a cartridge piercing body within a housing and a valve body in the housing spaced apart from the piercing body. A gas delivery tube extends from the piercing body to the valve body. A reservoir is formed by the valve body and the housing, and the gas delivery tube has a bleed hole opening into the reservoir. A pilot valve is substantially disposed in a pilot valve chamber in the valve body and a main valve piston is slidably positioned within the housing. The main valve piston sealingly engages against a liner seat on a liner. The main valve piston faces an annular chamber on one side with the annular chamber connected to the reservoir via a gas passageway. A main valve piston chamber on the other side of the main valve piston is connected to the pilot valve chamber. The pilot valve is actuatable to vent the pilot valve chamber. This causes the main valve piston to separate from the liner seat such that compressed gas from the reservoir flows past the main valve piston into a plunger chamber to rapidly drive a plunger into a medication ampule for needleless injection through the skin.

These and other related objects are also achieved according to the invention by an injection device having a trigger actuatable by the user of the device to open the pilot valve. A slide is axially displaceable on the device between a first slide position wherein the slide interferes with and prevents actuation of the trigger, and a second slide position wherein the slide is removed from the trigger to allow actuation thereof.

A spring is provided to bias the slide towards the first slide position. A detent collar is provided within a retainer in the slide. The collar is rotatable within the retainer between a first or locked position and a second or unlocked position. A first locking system including a link in the retainer biased into the collar locks the collar in the locked position. The first locking system is unlocked when an ampule having a key tab is inserted into the device with the key tab extending into a slot in the collar and in alignment with the link. A second locking system including a groove on the slide and a detent collar follower locks the slide into a first slide or slide locked position. The second locking system can be unlocked for actuation of the device only with the detent collar in the second or unlocked position. The device may then be actuated with the user pushing the slide forward and then depressing the trigger.

In a method of intermuscular and subcutaneous injection, an ampule is secured on an ampule receptacle thereby unlocking an ampule detecting interlock. A trigger interlock is disabled or unlocked and a valve is actuated to release compressed gas to drive an injectant out of the ampule.

These and other related objects are further achieved according to the invention by an injection device having a housing, a pilot valve connectable to a compressed gas source, a main valve operatively connected to the pilot valve, and a detent assembly for locking and unlocking a trigger which opens the pilot valve. Preferably, the detent switch assembly includes a slide block having a slide block pin which can engage the trigger.

The ampule preferably comprises a generally cylindrical body having ampule walls which form an injectant chamber. A throat extends and tapers from the injectant chamber to a nozzle at one end of the ampule. Cam flanges are provided at the other end of the ampule for securing the ampule to the injection device. Key tabs on the ampule adjacent and perpendicular to the flanges is provided for disengaging the first locking system of the injection device.

The ampule most desirably also has a generally cylindrical injectant chamber and a transition zone having a concave section adjoining the injectant chamber. A convex section adjoins the concave section and a conical section adjoins the convex section. A nozzle at the front end of the ampule adjoins the conical section to reduce pressure losses and lower turbulence.

BRIEF DESCRIPTION OF THE DRAWINGS

Other objects and features of the present invention will become apparent from the following detailed description taken in connection with the accompanying drawings. It is to be understood, however, that the drawings are designed for the purpose of illustration only and are not intended as a definition of the limits of the invention.

In the drawings wherein similar reference characters denote similar elements throughout the several views:

FIG. 1 is a perspective view of the present needleless injection device in the ready for injection state;

FIG. 2 is a side view in part section of the injection device of FIG. 1;

FIG. 4 is an enlarged section view taken along line 4—4 of FIG. 3;

FIG. 5 is a top interior view taken along line 5—5 of FIG. 4;

FIG. 6 is a side view of the Luer fitting provided on the ampule shown in FIGS. 2 and 7; and FIG. 7 is an enlarged section view fragment of an ampule which may be used with the injection device.

FIG. 8 is a perspective view of a second embodiment of the present needleless injection device in the ready for injection state;

FIG. 9 is an enlarged side view in part section of the injection device of FIG. 8;

FIG. 10 is a front elevation view taken along line 10—10 of FIG. 9;

FIG. 11a is an enlarged fragment view in part section of certain features of the device of FIG. 8;

FIG. 11b is an enlarged fragment view in part section of certain features of the device of FIG. 8 while the device is injecting;

FIG. 18 is a front elevation view of the ampule of FIG. 16;

FIG. 19 is a rear elevation view of the ampule of FIG. 16;

FIG. 20 is a section view of the ampule taken along line 20—20 of FIG. 19;

FIG. 21 is a front elevation view of an adapter plate to facilitate use of existing ampules with the device of FIG. 8;

FIG. 22 is a bottom elevation view of the adapter plate of FIG. 21;

FIG. 23 is a side elevation view of the adapter plate of FIG. 21 on an existing ampule;

FIG. 24 is an enlarged front elevation view in part section of the collar of FIG. 16;

FIG. 25 is a section view of the collar taken along line 25—25 of FIG. 24;

DETAILED DESCRIPTION OF THE PREFERRED EMBODIMENTS

Figure 3:
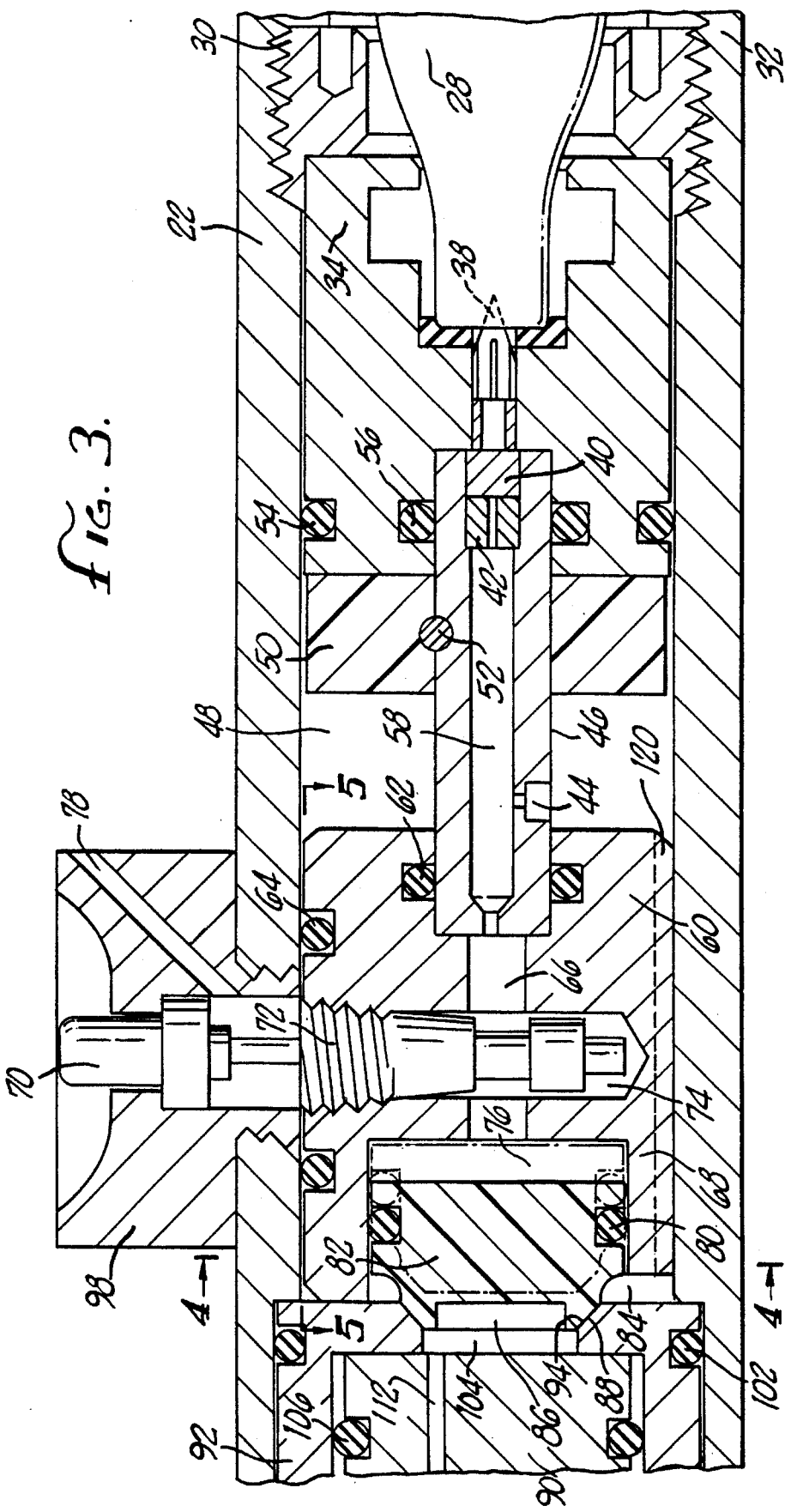
FIG. 3 is an enlarged fragment view in part section of the valve mechanisms and gas delivery system of the device of FIG. 2.
Figure 12:
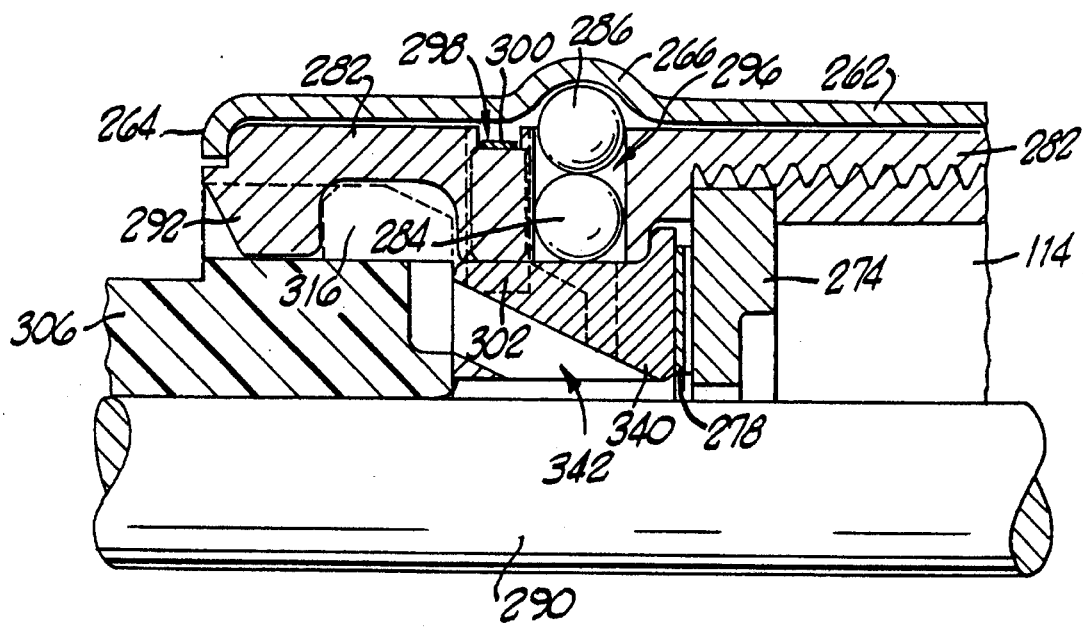
FIG. 12 is an enlarged fragment in part section of the device of FIG. 8 with a first locking system of the device unlocked by an ampule secured to the device.

Referring now in detail to the drawings, therein illustrated is a novel needleless hypodermic injection device, which as shown in FIGS. 1 and 2 includes a housing 22 and a cartridge holder 24 threaded onto an internal threaded section 32 of the housing 22 and holding a cartridge 28. At room temperature, the cartridge 28 contains a saturated gas/liquid, such as $CO_2$ or some other appropriate pressure medium, hereinafter referred to as "compressed gas". An opening 26 is provided in the cartridge holder 24. A spanner collar 30 is threaded onto the internal threaded section 32 of the housing 22 ahead of the cartridge holder 24 and serves to hold other internal components in place.

Turning to FIG. 3, a piercing body 34 is contained within the housing 22 against the spanner collar 30. An elastomeric washer 36 within the piercing body seals against the facing end of the cartridge 28. A slotted piercing pin 38 extends outwardly from the piercing body 34 into the cartridge 28. The piercing pin 38 connects to a gas delivery tube 46. A filter 40 and an orifice 42 are secured within the gas delivery tube 46.

Spaced apart from the piercing body 34 within the housing 22 is a valve body 60. The valve body 60, housing 22, and piercing body 34 form a reservoir 48 around the gas delivery tube 46. A bleed hole 44 leads from the gas delivery tube to the reservoir 48. A spacer 50 is optionally secured around the gas delivery tube 46 within the reservoir 48 by a pin 52.

An O-ring 54 seals the piercing body against the inner surface of the housing 22. Similarly, an O-ring 56 seals the gas delivery tube 46 to the piercing body 34.

At the other end of the gas delivery tube 46, an O-ring 62 seals the gas delivery tube 46 to the valve body 60, with the gas delivery tube extending into a bore 66 running through the valve body 60. A pilot valve 72, preferably a Schrader-type valve, is contained within a pilot valve chamber 74 within the valve body 60. The valve body 60 includes a sleeve section 68 substantially containing a main valve piston 82. An O-ring 80 seals the main valve piston 82 against the inner surfaces of the sleeve section 68 of the valve body 60 with the main valve piston 82 slidably disposed therein. In between the main valve piston 82 and the pilot valve chamber 74 is a main piston chamber 76, with the bore 66 also extending from the pilot valve chamber 74 to the main piston chamber 76. As shown in FIG. 4, gas passageways 120 extend along the periphery of the valve body 60 to connect the reservoir 48 to an annular chamber 84. The gas passageways 120 are designed to maximize unrestricted flow from the reservoir 48 into the plunger chamber 114.

The main valve piston 82 includes a piston face 88 for sealing against a valve or liner seat 94 of a liner 92. Alternatively, the seat may be formed on an inwardly extending annular rim section of the housing 22. The main valve piston 82 and liner seat 94 form the main valve of the injection device. The main valve piston 82 is advantageously made of TEFLON and also preferably has a counter bore 86 for improved sealing characteristics.

A button 70 is held against the pilot valve 72 within a button housing 98. An O-ring 64 seals the valve body 60 to the inner surface of the housing 22, around the pilot valve 72 which passes partially through the housing 22. A vent 78 extends through the button housing 98 into the pilot valve chamber 74.

The liner 92 has an opening 104 adjacent the liner seat 94 and is sealed against the inner surface of the housing 22 by O-ring 102. The sleeve section 68, the liner 92 and the main valve piston 82 form a seat chamber or annular chamber 84 on the side of the main valve piston 82 opposite of the main piston chamber 76.

Within the liner 92 is a plunger driver 90 engaging a plunger 96. A plunger driver orifice 112 extends through the plunger driver 90 connecting the liner opening 104 to the plunger chamber 114. As shown in FIG. 2, a compression spring 116 is positioned on a hub 118 extending into the plunger chamber 114. The spring 116 biases the plunger driver 90 against the end of the liner 92 adjacent the liner seat 94. An O-ring 106 seals the plunger driver 90 against the liner 92.

Referring now to FIG. 7, a threaded collar 102 having a vent 122 leading to the plunger chamber 114 joins the housing 22 and a threaded end 128 of an ampule holder 130. Within the ampule holder 130 is an ampule 132 having a base 146 abutting the threaded collar 102. The conically tapered inner surface of the ampule holder 144 matches the conically tapered outer surface 142 of the ampule 132, to support the ampule walls 152 all around. With shallow angles of taper, there is a tendency for the ampule 132 to stick in the ampule holder 130 after the injection. This is called a locking taper. The ampule 132 and ampule holder 130 preferably have approximately a 16 degree taper which is advantageously above the locking taper range. The ampule 132 is advantageously a single molded piece. A breech lock fitting may alternately be provided for quick ampule replacement.

The plunger 96 has a tapered end 124 and a seal 126 extending into an injectant chamber 134 within the ampule 130. The plunger seal 126 seals the plunger 124 against the injectant chamber walls 136, which are substantially parallel. The injectant chamber 134 leads to a flow path comprising a first transition 138 extending into a throat 140 leading to a second transition 149 and a nozzle 148. The flow path smoothly makes the cross section area reduction from the injectant chamber 134 to the nozzle 148, to minimize flow losses. Around the outside of the nozzle end of the throat 140 of the ampule 132 is an ANSI standard Luer fitting 150 as detailed in FIG. 6. This fitting permits connection of the ampule 132 to another medical device or container in a leak proof and mechanically secure manner. Advantageously, an ampule 132 made of or lined with glass or another material which does not interact with the desired injectant may be used. The injectant chamber 134, first transition 138, throat 140, second transition 149 and nozzle 148 are preferably molded in as part of the ampule during its manufacture.

A shield 160 is preferably provided over the ampule 132 and at least part of the ampule holder 130. The shield 160 includes a Luer sleeve 168 adapted to fit over the Luer fitting 150 of the ampule 132. The front surface 162 of the shield 160 has ridges 164. A cylindrical flange 166 extends back from the front surface 162 and engages the ampule holder 130.

In operation, the cartridge holder 24 is unscrewed from the housing 22 of the injection device 20. A compressed gas cartridge 28, such as a $CO_2$ cartridge is placed into the cartridge holder 24. The cartridge holder 24 is then threaded back onto the internal threaded section 32 of the housing 22. As the cartridge holder 24 is turned to engage the housing 22, the face end of the neck of the cartridge 24 engages, compresses and seals against the elastomeric washer 36 and the cartridge 28 is pierced by the piercing pin 38 projecting from the piercing body 34. After the cartridge 28 is pierced, compressed gas flows by the piercing pin 38, through the filter 40 and the orifice 42. The filter 40 traps any contaminants in the gas flow. The orifice 42 limits the flow rate.

Compressed gas flows through the orifice 42 and fills the duct 58 within the gas delivery tube 46. The gas continues to flow and fill the bore 66, pilot eve chamber and the main piston chamber 76. Simultaneously, gas flows from the duct 58 through the bleed hole 44 in the gas delivery tube 46 to fill the reservoir 48. From the reservoir 48 the gas flu through the gas passageways 120 to fill the annular chamber 84. After a sufficient interval, all chambers, spaces and flow channels are at a pressure P1.

The spacer 50 is provided in the reservoir 48 to allow the volume of gas contained in the reservoir to be varied. This capability of varying volume enables the device to be used for subcutaneous (usually relatively smaller volumes) and intramuscular (relatively larger volumes) injection. The bleed hole 44 is positioned adjacent to the valve body 60 such that a wider spacer 50 may be provided without interfering with the bleed hole 44. The diameter of the bleed hole 44 is small in comparison to the flow areas of the duct 58, bore 66 and gas passageways 120.

With device in the ready state, as described above and as illustrated in FIG. 3, the piston face 88 of the main valve piston 82 is sealed against the liner seat 94 of the liner 92, such that no gas may flow through the liner opening 104. The main valve piston 82 is forced against the liner seat 94 to make the seal by virtue of the pressure exerted on the back of the main valve piston, i.e., the surface facing the main piston chamber 76. Although in the ready state, the annular chamber 84 and in the main piston chamber 76 have equal gas pressure, the projected area of the main valve piston 82 facing the main piston chamber 76 is greater than the projected area of the main valve piston 82 facing the annular chamber 84. The resulting force imbalance causes the main valve piston 82 to be tightly sealed against the liner seat 94.

Using known techniques, the desired injectant is loaded into the ampule 132. Single-use ampules may be provided as a unit along with the plunger 96 and the shield 160. Unit-dose ampules prefilled with injectant may also be used. These ampules have a relatively larger surface around the nozzle 148 and no Luer fitting. Correspondingly, the throat 140 of such ampules may be shortened. The base 146 of prefilled ampules is sealed with a plug or membrane.

With the ampule 132 loaded with injectant, the ampule holder 130 is placed over the ampule 132 and the threaded end 128 of the ampule holder 130 is engaged by the threaded collar 102. The plunger 96 passes through the threaded collar 102 and extends into the plunger driver 90 in the plunger chamber 114. (See FIG. 2.) The injection device is then ready for injection, by placing the device 20 against the patient's skin. (See FIG. 1).

As the front surface or the ampule 132 is relatively small, the shield 160 advantageously is provided over the Luer fitting 150 of the ampule 132 to help steady the injection device 20 against the patient's skin. The ridges 164 on the front surface 162 of the shield 160 help to prevent sliding over the patient's skin and local anesthetic phenomenon. The flange 166 of the shield 160 covers the ampule holder surface 30 and is intended to help to prevent bodily fluids from contacting the reusable ampule holder 130.

During the injection sequence, substantial pressure is developed within the injectant chamber 134. Consequently, it is advantageous to avoid overstressing the injectant chamber walls 136. The ampule holder 130 may help to prevent excessively stressing the Luer fitting 150, the transition 138 or the injectant chamber walls 136 of the ampule 132 by at least partially transferring stresses (which may be generated by lateral or bending movement of the nozzle 148 against the patient's skin) to the ampule holder 130.

With the device 20 in the ready state and held against the patient's skin, the device 20 is activated by depressing the button 70. This causes the pilot valve 72 to open permitting the compressed gas in the pilot valve chamber 74 to escape through vent 78 to the outside. Simultaneously, the gas in the main piston chamber 76 rushes outwardly along the same path causing a substantial pressure drop therein. The small diameter of the bleed hole 44 in the gas delivery tube 46 severely restricts the flow of gas from the annular chamber 84 through the gas passageways 120 and reservoir 48 into the duct 58. Similarly, the orifice 42 severely restricts the flow of gas from the cartridge 28. As a result, at the instant just after the button 70 is depressed, the pressure in the annular chamber 84 is far higher than the pressure in the main piston chamber 76. The main valve piston 82 is thereby rapidly driven in a snap action backwards towards the pilot valve chamber 74 such that the seal between the piston face 88 and the liner 94 is opened, as shown in phantom in FIG. 3. The gas in the reservoir 48 is then able to flow through the gas passageways 120 and through the opening 104 into the plunger chamber 114 to drive the plunger driver 90 and plunger 96 into the injectant chamber 134 of the ampule 132. As the plunger 96 and plunger driver 90 move outwardly toward the ampule 130, the plunger chamber 114 is vented through the plunger chamber vent 122. The rapid acceleration of the plunger 96 causes the injectant to be injected out of the nozzle 148 at a pressure and velocity sufficient to pass through the patient's skin.

During the injection sequence, a small amount of compressed "bleed" gas may also flow from the cartridge 28 and reservoir 48 into the pilot valve chamber and out through the vent 78. However, this quantity of gas is acceptably small in comparison to the "driving" gas flowing from the reservoir 48 into the plunger chamber 114. In addition, since the volume of the reservoir 48 is large compared to the initial "dead" volume between plunger driver 90 and the main valve, the rise in gas pressure acting on the plunger driver 90 is very fast.

Following the injection, the button 70 is released and the pilot valve 72 closes. The gas pressures in the various ducts and chambers within the housing 22 then once again equalize and return substantially to P1. Specifically, compressed gas from the cartridge 28 flows through the bleed hole 44 to repressurize the reservoir 48 and through the duct 58 to repressurize the bore 66 pilot valve chamber 74 and main piston chamber 76. Due to the small size of the openings in the orifice 42 and the bleed hole 44, this repressurization occurs slowly in comparison to the injection sequence. As the main piston chamber 76 is repressurized, the main valve piston 82 is driven forward so that the piston face 88 once again seals against the liner seat 94. In the plunger chamber 114, the spring 116 pushes the plunger driver 90 back against the opening 104. As the plunger driver 90 is returned to its original ready position, remaining gas in the plunger chamber 114 vents through the plunger driver orifice 112.

To prepare the device 20 for the next injection, the ampule holder 130, the ampule 132 and the plunger 96 are removed from the housing 22 by unscrewing the ampule holder 130 from the threaded collar 102. A new ampule assembly 100 consisting of a new filled ampule 132, plunger 96, and shield 160 are installed on the device 20 as previously described.

Depending upon the particular application, the gas cartridge 28 is sufficient for several injections. To replace the cartridge 28 after a predetermined number of injections, the cartridge holder 24 is unscrewed from the housing 22. As the cartridge holder 24 is being unscrewed from the housing 22, remaining compressed gas in the cartridge 28 may escape from the cartridge 28 into the interior of the cartridge holder 24. The opening 26 at the end of the cartridge holder 24 prevents the cartridge holder 24 from becoming pressurized, such that the cartridge holder 24 may be easily removed from the housing 22. A new gas cartridge 28 is then installed as previously described.

The device 20 may be used for intramuscular or subcutaneous injections. For subcutaneous injection, the nozzle 148 has a relatively smaller opening and the reservoir 48 is largely occupied by a spacer 50, limiting the gas volume therein to preferably as little as 20% of the full reservoir volume. For intramuscular injection, a larger nozzle 148 opening is advantageously used and the reservoir may be up to 100% filled with "driving" gas, i.e., no spacer is used. The nozzle 148 opening may range in diameter and spacer 50 size (or length) determine whether the device is set up for intramuscular or subcutaneous injection.

Various other design alternatives will be apparent to those skilled in the art. For example, the various O-rings which seal non-moving components within the housing 22 may be replaced or eliminated by other types of seals (including adhesives) or internal construction. In addition, a diaphragm or bellows could be used in place of the main valve piston 82 and various other configurations of the valves, chambers and flow passageways are also possible.

FIGS. 8–25 illustrate a second embodiment of the injection device and an ampule for use with this device. The second embodiment includes a compressed gas pressure indicator and interlock systems.

Referring to FIGS. 8, 9 and 10, the second embodiment of the device 200 has a tubular housing 205 containing substantially the same elements as shown in FIG. 3. The structure and operation of these elements within the housing 205 are substantially the same as those described above and illustrated in FIG. 2–5. A gas cartridge holder 226 holding a cartridge 28 is threaded on to the back or cartridge end of the housing 205. A thumb screw 228 is threaded through the cartridge holder 226 and extends into the cartridge chamber 225. A vent 229 extends through the cartridge holder 226.

Referring specifically to FIG. 9, a slide assembly 201 having a slide tube 202 is fitted over the housing 205. A trigger 204 is pivotally mounted onto the housing 205 by a trigger pin 206 and protrudes through the top of the slide assembly 201.

Referring now to FIG. 11a, the slide assembly 201 has a ramp 209 extending at an incline up to a trigger opening 220 in the slide tube 202. A thumb rest 208 of the trigger 204 extends through the trigger opening 220. A planer trigger anvil 214 on the trigger 204 is positioned over a pilot valve pin 216 for actuating a pilot valve 218. The trigger 204 has a trigger slot 210. A slide overhang 222 of the slide tube 202 has a trigger stop 212 extending into the trigger slot 210. The trigger stop 212 prevents the trigger 204 from depressing the pilot valve pin 216 to actuate the pilot valve 218, except when the device is unlocked during an injection.

Forward of the trigger 204 is a compressed gas pressure indicator assembly 230. The indicator assembly includes a Bourdon tube 238 having an open end extending into an adaptor 242 threaded into an end cap 250 which is sealed against a flattened portion of the housing 205 with an O-ring 246. The other side (top) of the end cap 250 is spaced apart from the slide tube 202 by a slide bushing 245. An O-ring 244 seals the adaptor 242 against the end cap 250. Similarly, an O-ring 224 seals the pilot valve 218 against the inside surface of the housing 205. A spring cup 252 surrounding the adapter 242 supports the back end of a compression spring 240. The compression spring 240 extends forward over the Bourdon tube 238 to a barrel 254 substantially surrounding an indicator cylinder 231. The indicator cylinder 231 is provided with a flag 236 having two different colored sections 235 and 237, for example red and green. The two colored sections 235 and 237 are separated by a demarcation line 243.

A shaft 258 extends from the indicator cylinder 231 through a rotation bushing 256. An end support 234 mounted to the housing 205 supports the rotation bushing 256. A window 232 made of a transparent material is provided in the slide tube 202 over the indicator cylinder 231. The window 232 is preferably provided with an axially extending reference line.

Referring to FIGS. 9 and 11a, the open end 239 of the Bourdon tube connects to an opening 241 extending through the adaptor 242 and to a duct 248 passing through the bottom wall of the adaptor 242 and through the housing 205. As shown in FIG. 9, a duct extension 249 connecting to the duct 248 passes through the valve body 60 to the pilot valve chamber 219.

Referring to FIG. 11a, a bridge radius 260 extends from the slide tube 202 overlying the indicator assembly 230 and is joined to a forward extension 262 of the slide tube 202. As shown in FIGS. 9 and 11a, the forward extension 262 of the slide tube 202 has a lock groove 266 forward of the connection to the bridge radius 260. An inwardly extending rim 264 is provided at the other end of the forward extension 262.

Figure 16:
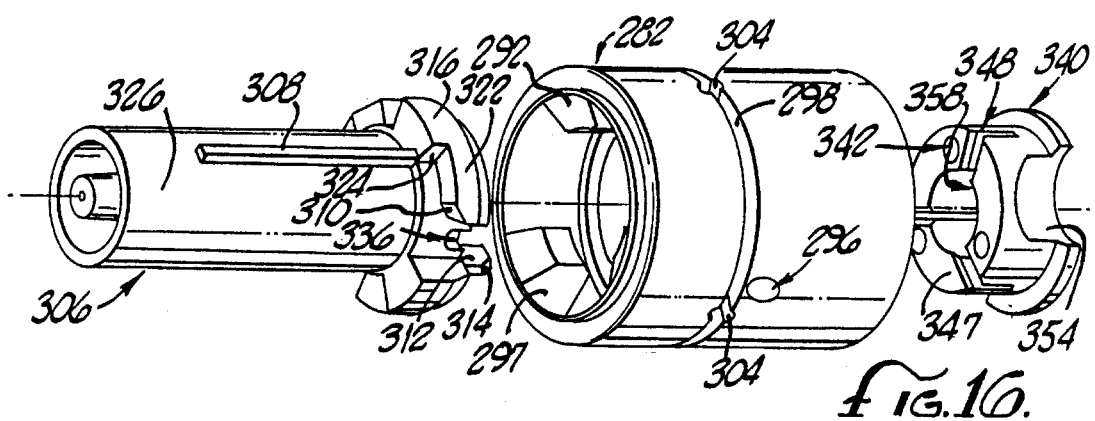
FIG. 16 is an exploded perspective view of an ampule, a retainer and a detent collar of the device of FIG. 8.

A retainer 282 within the slide tube 202 has three equally radially spaced apart hooks 292 (see FIG. 16). A threaded end of the retainer is screwed onto a threaded end 272 of the housing 272, with the retainer shoulder 289 clamping the end support 234 against the housing 205. A plunger chamber end cap 274 is secured in between a retainer boss 275 and the threaded end of the housing 272. A detent collar 340 is held in place within the retainer 282 with a detent collar ring 341 slidably held against the retainer boss 275 by a wavy spring 278.

As illustrated in FIGS. 16, 24 and 25, the detent collar 340 has a cylindrical collar surface 356 interrupted by three equally radially spaced apart crescents 352 extending forward from the detent collar ring 341 to approximately the midpoint of the length of the detent collar 340. In between the three crescent surfaces 354 are three equally radially spaced apart slots 348 extending from the front surface 347 of the detent collar 340 rearward the detent collar ring 341. Chamfered guides 350 are provided at the front surface of the detent collar 347 on either side of each slot 348. A collar plunger bore 358 extends axially and centrally through the detent collar 340. As shown in FIGS. 24 and 25, adjacent to each slot guide 350 is a link or slide pin socket 344. The sockets 344 extend just slightly into the collar surface 356. Pressure relief bores 342 extend through the detent collar 340 from the front surface 347 into the collar plunger bore 358.

Figure 14A:
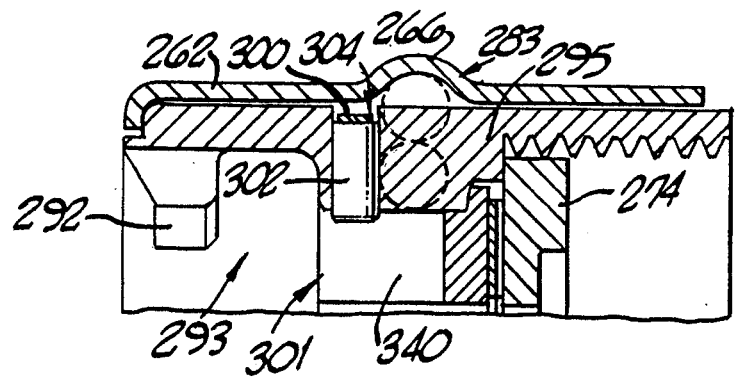
FIG. 14a is an enlarged fragment view in part section showing the front end of the device of FIG. 8 before an ampule is secured into the device.

The retainer 282, as shown in FIGS. 11a and 14a-3, has an ampule slot 293 in between the retainer hooks 292 and the retainer body 295. (In FIGS. 14a–c, the bridge radius and housing are omitted for clarity.) The detent collar 340 is positioned inside of the retainer body 295. As shown in FIG. 14a, slide pin holes 304 extend through the retainer body 295. Slide pins 302 within the holes 304 are radially biased inwardly onto the collar surface 356 of the detent collar 340 by a clock spring 300 overlying the slide pines 302 in a clock spring groove 298. The slide pins 302 are adapted to protrude into the link or slide pin sockets 344 on the detent collar 340, to reversibly lock the detent collar from rotation within the retainer 282. Various alternative collar-retainer link configurations to link or lock the detent collar from rotating in the retainer are feasible.

In the retainer body 295 behind the slide pin holes 304 is a detent collar follower indicated generally as 283. In the preferred embodiment, the detent collar follower 283 includes inner and outer balls 284 and 286 within three detent ball bores 296. The lower balls 284 rest on the collar surface 356 such that the outside balls 286 protrude into the lock groove 26 of the forward extension 262 of the slide tube 202. Other detent collar follower configurations including pins and expandable rings are also possible.

In use, a compressed gas cartridge 28 is first installed into the device 200. Specifically, the cartridge holder 226 is unscrewed from the housing 205 and a cartridge 28 is inserted into the cartridge chamber 28 with the thumbscrew 228 substantially backed out of the cartridge chamber 225. The cartridge holder 226 is then threaded back onto the housing 205 with the neck of the cartridge 228 facing the piercing pin 38 and the elastomeric washer 36 (see FIGS. 3 and 9). The thumbscrew 228 is then turned inwardly or forward to force the compressed gas cartridge 28 onto the piercing pin 38. Compressed gas then flows from the compressed gas cartridge 28 into the device as described above for the device of FIGS. 1–3.

As shown in FIGS. 11a and 14a, no ampule 306 is yet installed in the device 200 and the device 200 is in a locked condition. The trigger 204 cannot be depressed to actuate the pilot valve 218 because the trigger stop 212 holds the trigger anvil 214 away from the pilot valve pin 216. The trigger stop 212 cannot be pushed or slid forward out of the trigger slot 210 because the lock groove 266 on the forward extension 262 of the slide tube 202 interferes with and cannot pass over the outer ball 286 of the collar follower 283. The outer balls 286 are held in the "up" position into the lock groove 266 by the lower balls 284 which in turn are resting on the collar surface 356 of the detent collar 340. The detent collar 340 is held in position relative to the retainer 282 slide pins 302 biased into the slide pin sockets 344 on the detent collar 340, by the clock spring 300. Consequently, in this state, the crescents 352 on the detent collar 340 cannot be moved into alignment with the inner balls 284. Thus, with no ampule secured into the device 200, the device cannot be actuated and no compressed gas can be released.

Referring now to FIGS. 12, 13, 14b and 20, an ampule 306 containing an injectant in the injectant chamber 388 is inserted into the front end of the device 200 by pushing in and turning within the retainer 282. The radial tabs 312 on the back of the ampule 306 are aligned with the slots 348 in the detent collar 340. The flanges 316 of the ampule 306 pass in between the retainer hooks 292 as the ampule 306 is inserted.

Figure 13:
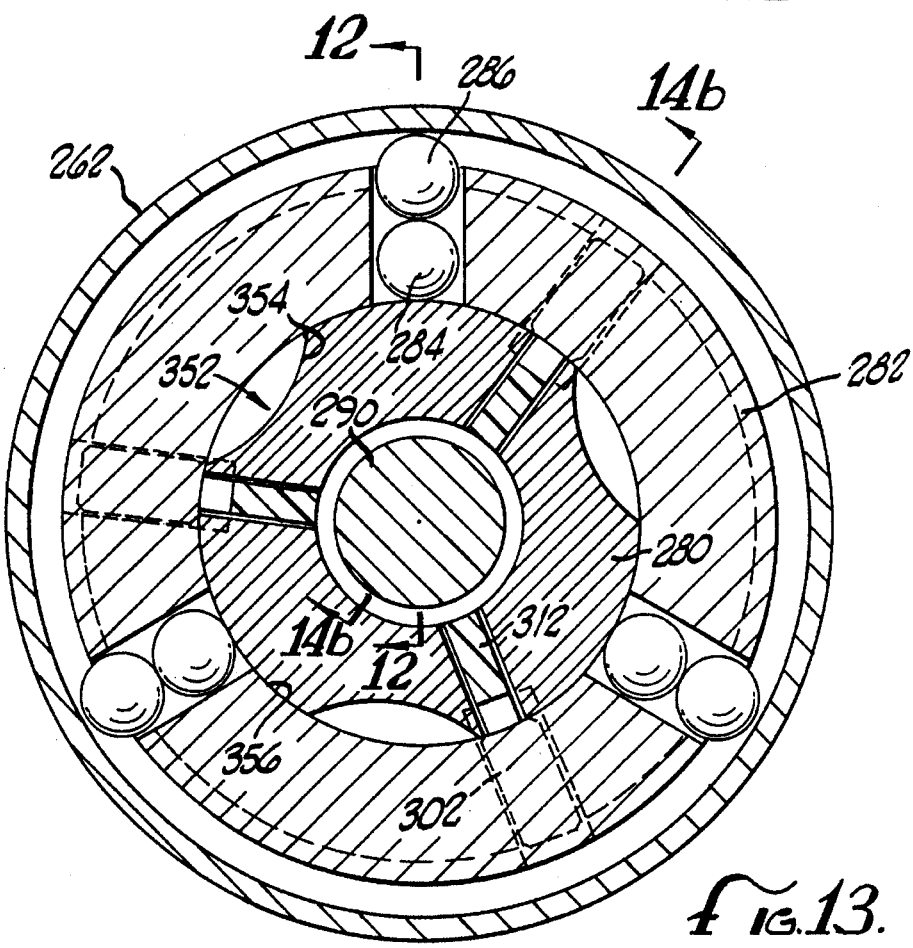
FIG. 13 is an enlarged section view taken along line 13—13 of FIG. 9.
Figure 14B:
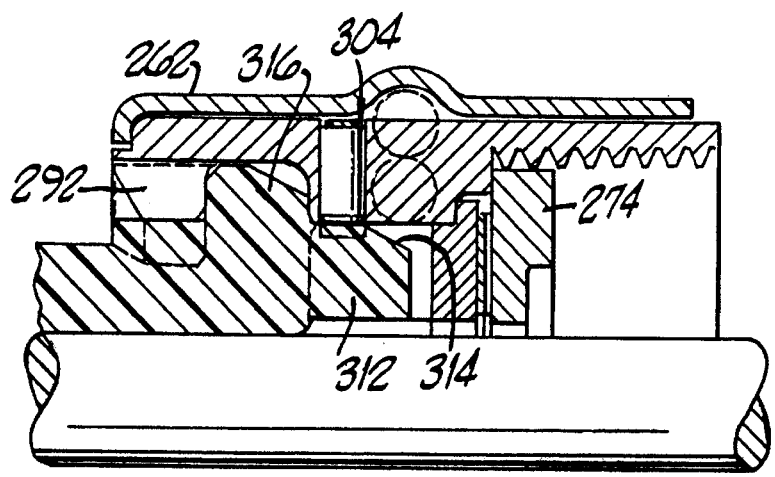
FIG. 14b is an enlarged fragment view in part section of the front end of the device of FIG. 8, as taken along line 14b—14b of FIG. 13 and showing an ampule installed but not secured into the device.

As the radial tabs 312 slide into the slots 348, the slide pins 302 ride up on the outside surfaces of the radial tabs 312 causing the slide pins 302 to lift out of the slide pin sockets 344. The detent collar 340 is then free to rotate within the retainer 282. This condition is shown in FIGS. 13 and 14b wherein the slide pins 302 (shown in phantom) are pushed out of the slide pin sockets 344 by the radial tabs 312 against the force of the clock spring 300. Although this link or slide pin locking system from locking the detent collar 280 to the retainer 282 is unlocked or disengaged, the device cannot be activated as the outer balls 286 still prevent forward movement of the slide tube 202 thereby preventing removal of the trigger stop 212 from the trigger slot 210.

The ampule 306 is then rotated along with the detent collar 340 within the retainer 282. The grip tab 308 on the ampule 306 provides a finger grip for gripping the ampule. While the ampule is turned it is also slightly pressed towards the back of the device 200 thereby compressing the wavy spring 278. The cams 310 on the cam arms 322 of the flange 316 on the back of the ampule 306 slide and wedge under the retainer hooks 292 (see FIG. 16).

Figure 14C:
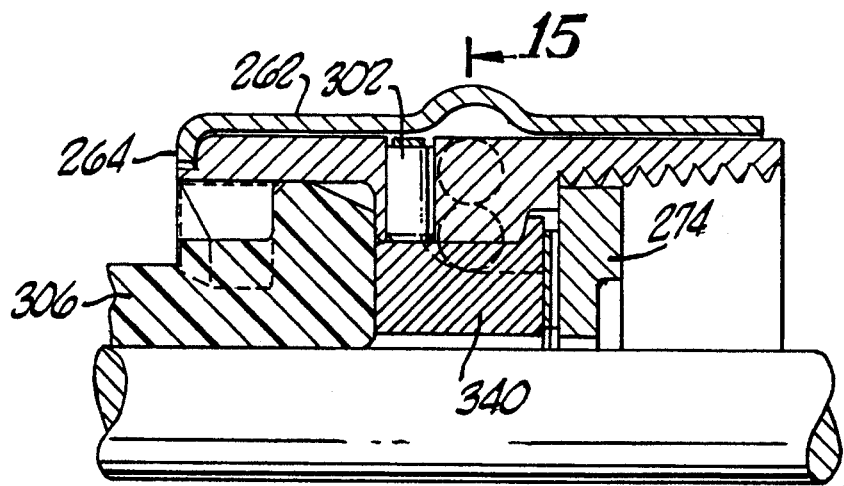
FIG. 14c is an enlarged fragment view in part section of the front end of the device of FIG. 8, with an ampule installed and secured into the device.
Figure 15:
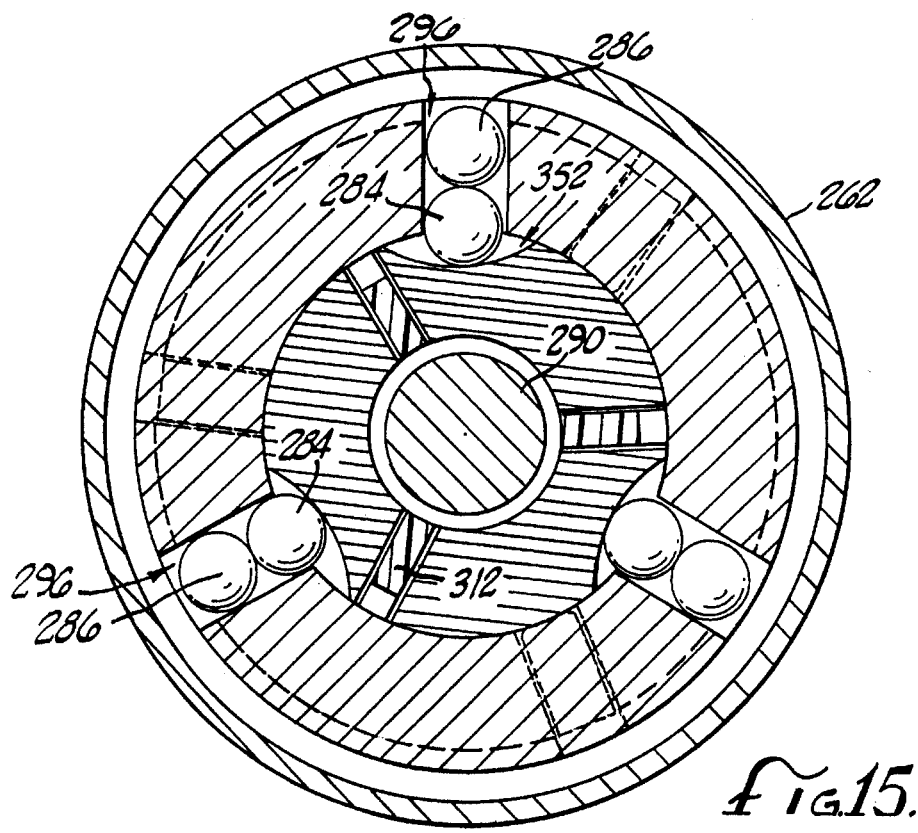
FIG. 15 is an enlarged section view taken along line 15—15 of FIG. 14c.
Figure 17A:
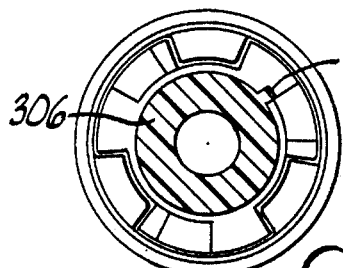
FIG. 17a is a front elevation view in part section showing the ampule inserted into the retainer of FIG. 16 but not secured therein.
Figure 17B:
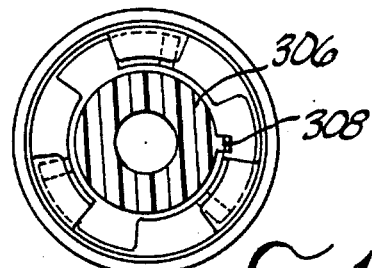
FIG. 17b is a front elevation view in part section showing the ampule rotated and secured into the retainer of FIG. 16.

The ampule 306 is turned until the stops 324 come to rest against the sides 297 of the retainer hooks 292, as shown in FIGS. 17a and 17b. As the detent collar 340 rotates with the ampule 306, the crescents 3564 come into alignment with the detent ball bores 296, thereby allowing the inner balls 284 to come to rest on the crescent surfaces 354. This allows the outer balls 286 to drop from the lock groove 266 as illustrated in FIGS. 14c and 15.

The link interlock 301 (comprising the biased slide pins 302 and sockets 344 for locking the detent collar 340 against rotation) and the collar follower interlock 283 (comprising the crescents 354 and balls 284 and 286 for preventing movement of the slide tube 202) have now both been unlocked or disabled. However, the slide tube 202 remains biased to the back of the device 200 by the compression spring 240. Consequently, the trigger stop 21 remains in the trigger slot 210 to prevent depression of the trigger 208.

To administer an injection, the device 200 is positioned with the nozzle and shroud 334 of the ampule 330 against the injection site on the patient. The user then slides the slide tube 202 forward with thumb or hand pressure on the ramp 209, overcoming the biasing force of the spring 240. This movement of the slide tube 202 and trigger 208 may be performed with one or two hands. As the slide tube 202 moves forward,the trigger stop 212 moves out of the trigger slot 210 allowing the trigger 208 to be fully depressed to actuate the injection sequence.

FIG. 11b illustrates the condition of the device 200 while injecting. The trigger stop 212 is temporarily displaced forward allowing the trigger 208 to pivot downwardly with the trigger anvil 214 depressing the pilot valve pin 216 to open the pilot valve 218. The elements within the housing 205 then operate as described above for the embodiment of FIGS. 1–3. The pressure relief bores 342 extending through the collar 340 and linking with the channels 336 in the ampule 306 provide a route to the outside of the device for relief of compressed gas exhausting from the plunger chamber 114 during actuation.

After the injection, the trigger 208 is released and biased to pivot away from the pilot valve pin 216. When the slide tube 202 is released by the user, the trigger stop 212 returns into the trigger slot 210. (FIG. 11a). The lock groove 266 moves back over the detent ball bores 296. The ampule 306 is rotated in the reverse direction along with the detent collar 340 and the ampule is removed from the device 200, thereby resetting or relocking the link and collar follower locking systems. The elements within the housing 205 correspondingly return to their original positions as described above with reference to FIGS. 1–3.

The indicator assembly 230 indicates whether the pressure of the compressed gas within the device 200 is sufficient for another injection. The Bourdon tube 239 is calibrated in a known manner to rotate with changes of pressure within the Bourdon tube 239. As shown in FIG. 9, the duct 248 and duct extension 249 connect the Bourdon tube 239 with the pilot valve chamber 219, such that the pressure in the Bourdon tube equals the pressure in the pilot valve chamber. As the pressure of the compressed gas in the device 200 decreases with each injection, the pressure within the Bourdon tube correspondingly decreases this causes the Bourdon tube 239 to turn the indicator cylinder. By looking through the window 232, the user the can view the flag 236 to determine if there is sufficient gas pressure for another injection. The bourdon tube 238 and indicator cylinder 231 are arranged so that when the gas pressure within the device 200 is sufficiently high, the green side 237 of the flag 236 appears in the window 232. As the gas pressure decreases, the indicator cylinder 231 turns with the red side 235 of the flag 236 gradually appearing in the window 230. When the red side 235 occupies a predetermined position in the window 232, the device no longer has sufficient pressure of another injection ad the cartridge 28 must be replaced.

The adapter plate of FIGS. 21–23 is used to operate the device with other ampules to having the key tabs 312.

Figure 26:
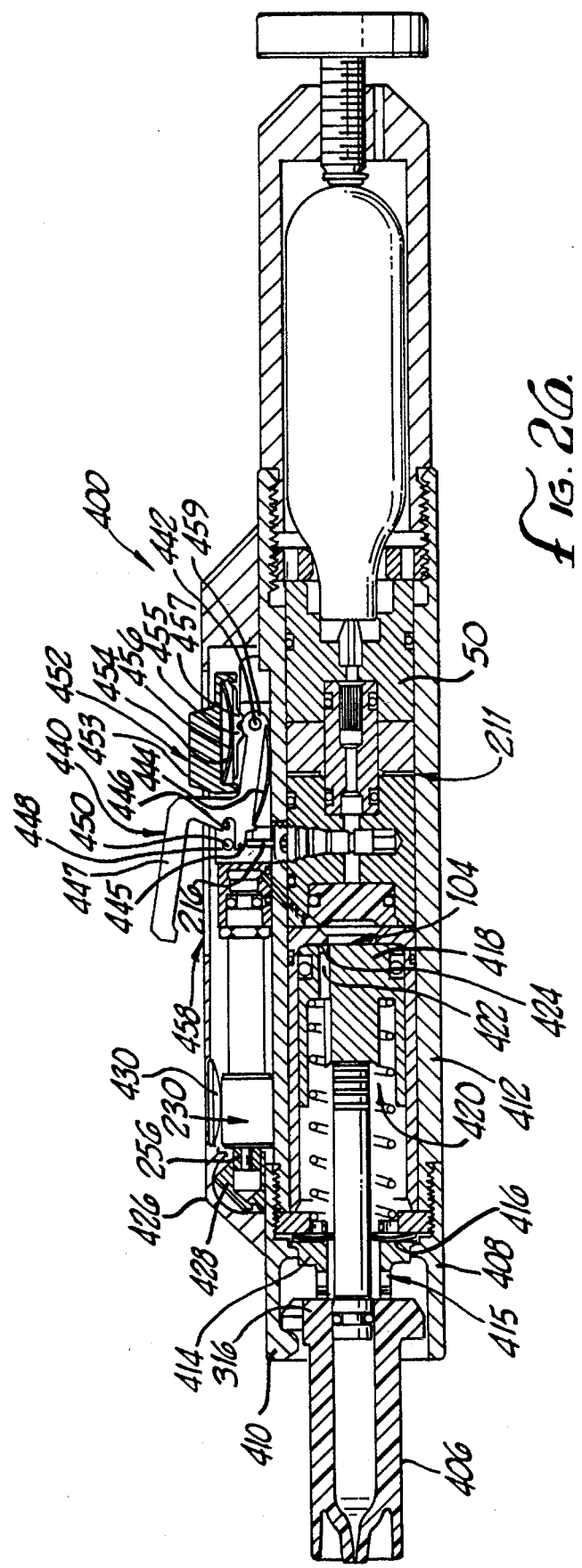
FIG. 26 is a section view of the a third embodiment of the present needleless injection device in the ready for injection condition.

FIGS. 26 illustrates a third embodiment of the present needleless injection device. As illustrated therein, an ampule 406 is secured to a retainer barrel 408 of a housing tube 412 of the injection device 400. Retainer hooks 410 to the retainer barrel 408 engage the flanges 316 of the ampule 406. A pressures plate 414 is biased by a wavy spring 416 against the back of the ampule 406 to secure it in place within the retainer barrel 408.

A plunger driver 418, similar to plunger driver 90, has a spring bore 420 and an eccentric vent 422 leading to an orifice insert 424 leading to the liner opening 104. The offset position of the eccentric vent 422 helps insure free return of the plunger driver 418 after injection.

Adjacent to the valve body 60, the spacer 50 leaves a very small volume reservoir 211, as the remaining compressed gas filling the spaces in the various chambers and passageways (which are the same as in the previous embodiment) provide adequate volume of compressed gas for injection.

An upper housing 426 is fixed in position on the outside of the housing tube 412, e.g., with screw fasteners and/or adhesives. An anchor bushing 4528 is attached to the outside of the housing tube 412 and is further secured in place by the upper housing 426. The anchor bushing 428 supports the rotation bushing 256. An enlarging window 430 is provided ont he upper housing 426 to permit viewing of the compressed gas pressure indicator assembly 230.

A trigger lever 440 is pivotally mounted to the housing tube 412 by a pivot pin 442. The trigger lever 440 has a locking slot 446 and an extension 447 extending through a cut out 458 in the upper housing 426. A leaf spring 444 biases the trigger lever 440 away from the housing tube 412. A boss 445 on the trigger lever 440 rests on top of the pilot valve stem 216. A slide block 448 is slidably mounted onto the housing tube 416. A slide block pin 450 extends from the slide block 448 and is engageable into the locking slot 446 of the trigger lever 440.

A detent switch assembly 452 is provided on the slide block 448. The detent switch assembly includes a detent button 453 extending through the cut out 458, a spring 444 and a detent plate 456 having protrusions 455 and 457 which are held against a detent surface 459.

Figure 27:
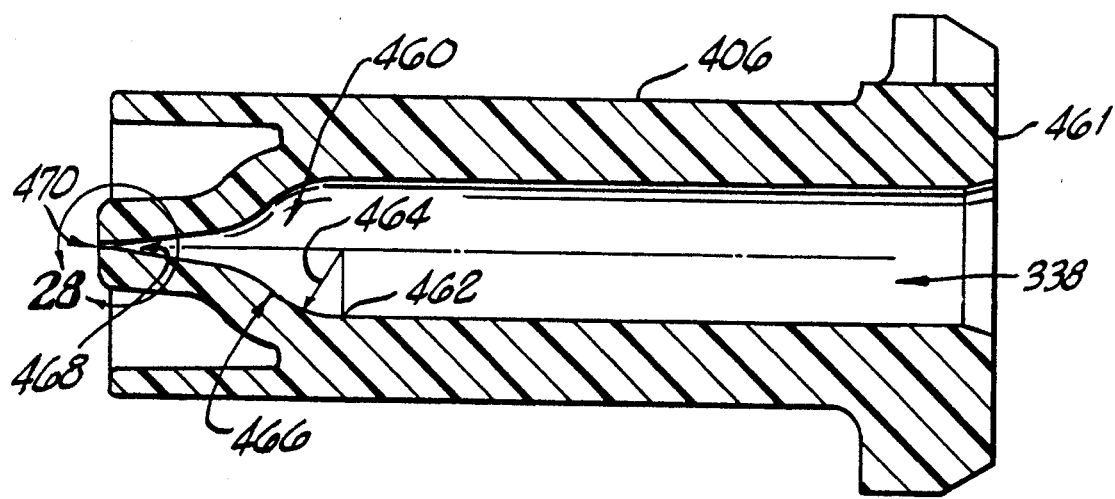
FIG. 27 is an enlarged section view of an ampule for use with the injection device of FIG. 26.

Referring to FIG. 27, the ampule 406 is similar to ampule 306 (FIG. 9) but has a generally flat rear surface 461 without tabs 312. These tabs are not required as the injection device of FIG. 26 does not have the ampule interlock system shown in the device of FIG. 9.

Figure 36:
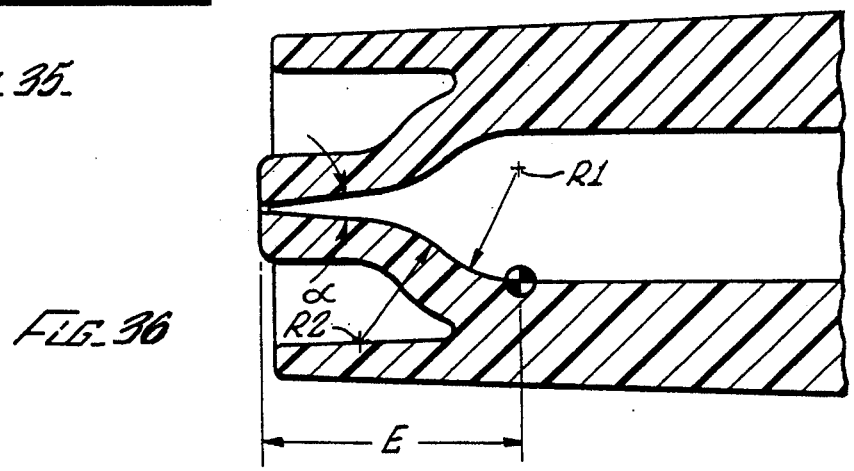
FIG. 36 is an enlarged view fragment of the nozzle end of the ampule of FIG. 27.

Referring once again to FIG. 27, the ampule, which is preferably injection molded as a single part of a polycarbonate such as clear LEXAN HP2, has an injectant chamber 338, a transition zone 460 and a nozzle 470. A first or concave radius 464 begins at a tangent point 462. A second or convex radius 466 adjoins the first radius 464. A conical taper 468 extends from the nozzle 470 to the second radius 466. This provides a smooth transition zone 460 between injectant chamber and nozzle to avoid stress concentrations in the ampule 406 and provide good injection characteristics. FIG. 36 shows preferred dimensions of the nozzle end of ampule 406, with R1 and R2 at 0.19 in., dimension E at 0.432 in. angle alpha at 14 degrees and an injectant chamber inside diameter of 0.250 in. nominal.

Figure 28:
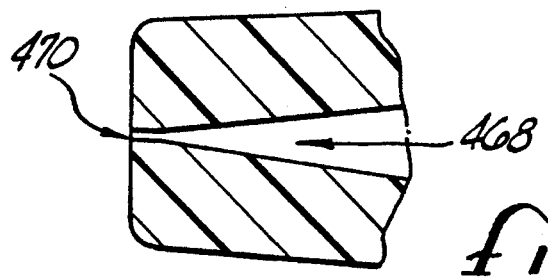
FIG. 28 is an enlarged section view fragment of the nozzle of the ampule of FIG. 27.

As shown in FIG. 28, the nozzle 470 extends a short distance before joining the conical taper 468. The nozzle diameter can vary, depending on application, e.g., intramuscular, subcutaneous, veterinarian, etc. FIG. 18 substantially illustrates the mounting tabs 316 of the ampule 406.

Figure 29A:
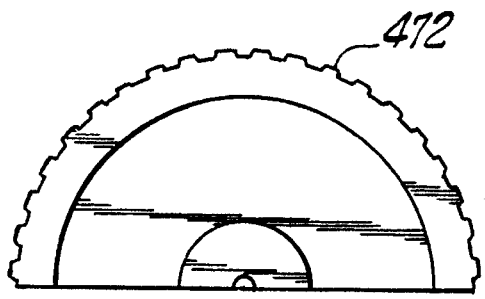
FIGS. 29(a) and 29(b) are enlarged views of the nozzle end of the ampule of FIG. 27.
Figure 29B:
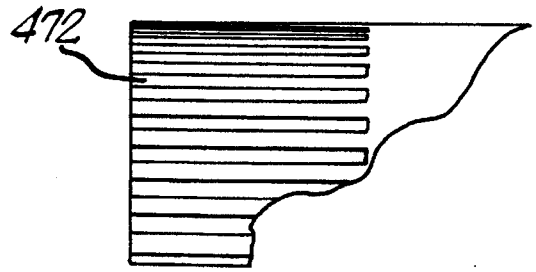

As shown in FIGS. 29a and 29b, the front portion of the shroud 334 of the nozzle 406 includes serrations 472 (instead of the finger block 308, as shown in FIG. 16) to provide a gripping surface.

In use, the ampule 406 is filled with injectant and is placed into the injection device 400 by passing the flanges 316 of the ampule 406 by the retainer hooks 410 on the retainer barrel 408. The pressure plate 414 is depressed slightly against the wavy spring 416. The ampule 406 is then rotated such that the flanges 316 engage the retainer hooks 410. The pressure plate 414 then clamps the ampule 410 in place within the retainer barrel 408.

The nozzle 470 of the ampule 406 is placed onto the injection site. The user pushes the detent button 453 forward, to switch the detent switch assembly from a locked to an unlocked position. As the detent button 453 is pushed forward, the slide block 448 slides forward and the slide block pin 450 disengages from the locking slot 446 on the trigger lever 440. The device 400 is then ready to inject. The trigger lever 440 is depressed to commence the injection sequence as previously described in the other embodiments. As the plunger 418 moves forward during the injection sequence, ambient gas in the plunger driver chamber is expelled by passing through relief holes 415 in the pressure plate 414, in between the flanges 316 of the ampule 406 and out of the front of the device 400.

After the injection, the spring 444 pushes the trigger lever 440 up, once it is released. The detent button 453 is returned to the locked position and the slide block pin 450 once again engages the locking slot 456 to prevent actuation of the device 400.

Generally, with hand power syringe/needles, the interior pressures are limited to a few psi, rarely or never exceeding about 30 psi. This limits the pressure producing forces on the ampule. Thus, the syringe can be thin-walled since stresses produced by the compressed injectant are low. On the other hand, with the compressed gas powered injection devices described herein, the pressures generated within the ampules may be orders of magnitude greater, i.e., in the range of approximately 3,000–6,000 psi. These higher pressures are necessary to generate a liquid jet with sufficient velocity to pierce the skin without a needle.

To achieve such a jet velocity that will pierce the skin at minimum pain levels, two basic jet characteristics should be provided:

1. The velocity profile across the jet diameter should be as flat as possible (not parabolic as in highly viscous tubular flow). This ensures that momentum of the jet will be sufficient, not only to initially pierce the skin, but also to momentum control depth of penetration.

2. Turbulence in the jet should be minimized to enhance axial momentum and additionally to minimize jet spreading due to turbulent transverse velocity components.

These characteristics can be achieved with proper nozzle design, in particular, the converging section between the larger cylindrical bore and the final cylindrical nozzle section. The converging transition should be without any rapid or step changes in cross-section. Long linearly tapered nozzles can provide characteristics 1 and 2 above. However, such designs have larger pressure losses, and are less practical for a disposable device since they use relatively large volumes of material. At the other extreme, a sharp edged hole in a perpendicular cylinder end can work as a nozzle but the resulting jet will generally not have characteristics 1 or 2 above. The preferred compromise, considering pressure losses versus characteristics 1 and 2 above and material requirements, is to have a short nozzle using connecting radii. This preferred design yields the least turbulence for given length.

To operate with the relatively higher injection pressures, the plunger 96 has a back-up ring 127 behind the O-ring 126, as shown in FIG. 7. In addition, the diameter of plunger 96 diameter is maximized to lower axial compressive stresses and for maximum resistance to column buckling within the space allowed.

Figure 30:
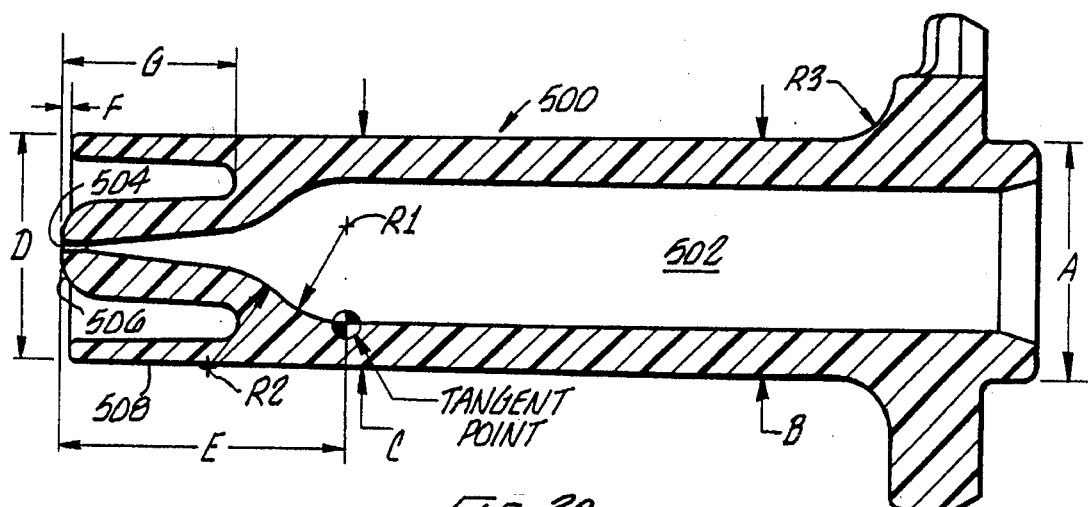
FIG. 30 is a section view of a third preferred ampule embodiment.
Figure 31:
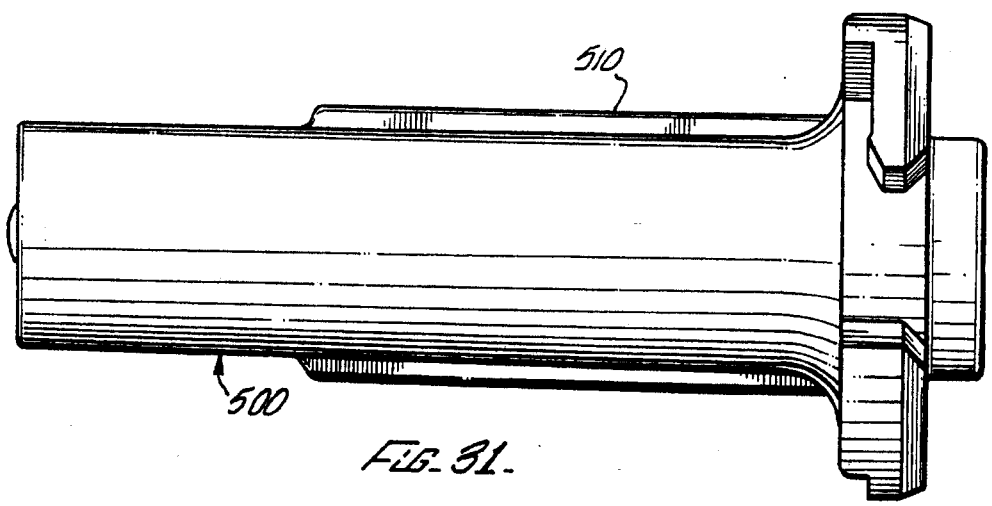
FIG. 31 is a side elevation view thereof.
Figure 32:
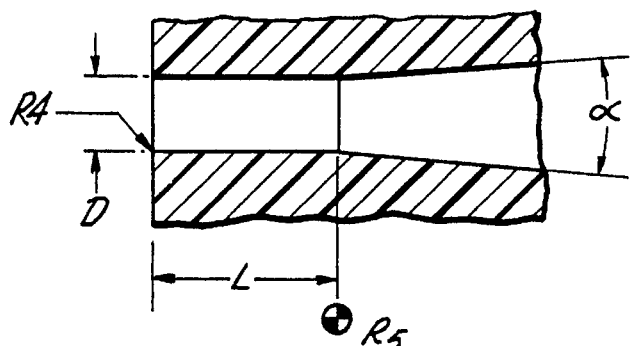
FIG. 32 is an enlarged view fragment of the nozzle of the ampule of FIG. 30.
Figure 34:
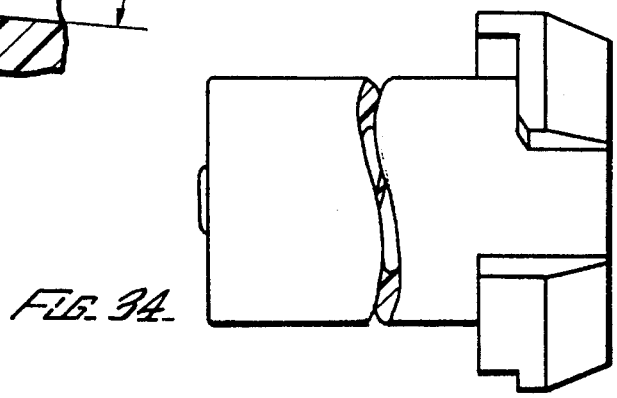
FIG. 34 is a side elevation view thereof.

The ampules shown in FIGS. 7, 20, 27 and 30–33 are designed to withstand the relatively higher injectant pressures generated during the injection sequence. One critical area in the ampule design is the Luer tip end. FIG. 32 depicts the nozzle and throat of the ampule shown in FIG. 27, as well as the ampule 500 shown in FIG. 30 and the ampule 600 shown in FIG. 33. Referring to FIG. 32, with a short nozzle length, the fluid cone angle alpha would conventionally be large, in the range of, for example, 20–30 degrees. In contrast, the standard Luer tip dimensions require a certain minimal axial length. The critical stress intensity occurs at the minimum section thickness, where the Luer taper transitions to the radius extending to the injectant chamber diameter. Thus, the fluid cone angle alpha must be reduced to keep stresses within safe limits. Resulting fluid cone angles (alpha) of 4–12 degrees are accordingly preferred, although these angles incur a small additional pressure drop.

Another stress concentration area of the ampules is at the rear or lug end. As shown in FIGS. 9 and 26, the ampules 306 and 406 (as well as the ampules of FIGS. 30–34) have three lugs which are attached to the injection device at the outer edge of the lugs. During injection, there is about a 200-pound axial load divided among the three lugs, in addition to the internal radial pressure loading on the ampule. This axial load causes high stress intensities at the corners where the lugs attach to the cylindrical ampule body. Accordingly, the lugs preferably have a gradual change in cross-section and a relatively large radius (for example, 0.093 in.) joining the lugs to the ampule body, as shown at R3 in FIG. 30.

Since the ampules are preferably disposable, their cost is minimized by reducing the material required for each ampule. Sufficient material must nevertheless be provided to maintain stresses at acceptable levels. Ampule 500 shown in FIG. 30 illustrates an ampule similar to ampule 27 but manufactured using less material.

Referring still to FIG. 30, the preferred contour design of the transition from the injectant chamber 502 of the ampule 500 to the nozzle 504 is defined by the concave radius R1 and convex radius R2, preferably both 0.19 inch. The nozzle end 506 of the ampule 500 protrudes by dimension F, preferably 0.020 inch beyond the ends of the shroud 508. This protrusion facilitates secure engagement of the nozzle against the patient's skin. The shroud length indicated by dimension G is preferably 0.310 inch and the dimension E from the tangent point to the nozzle is preferably 0.501 inch. The base or lug end diameter A is preferably 0.420 in. The wall thickness most desirably ranges from 0.084 near position B where the ampule outside diameter is 415 in., to 0.075 at position C where the ampule outside diameter is 0.402 in. With a total overall ampule length of 1.720 in., the spacing between positions B and C is preferably 0.823 in., with position B 0.370 in. from the lug end of the ampule. The injectant chamber diameter 502 nominally has a preferred diameter of 0.250 in. The ampule is designed for manufacture by injection molding and has appropriate draft angles. The nozzle end of ampule 500 is configured to the standard male Luer fitting. The angle alpha is preferably 10 degrees. As shown in FIG. 31, the ampule 500 has a series of radially extending ridges 510 to facilitate gripping the ampule by hand.

Figure 33:
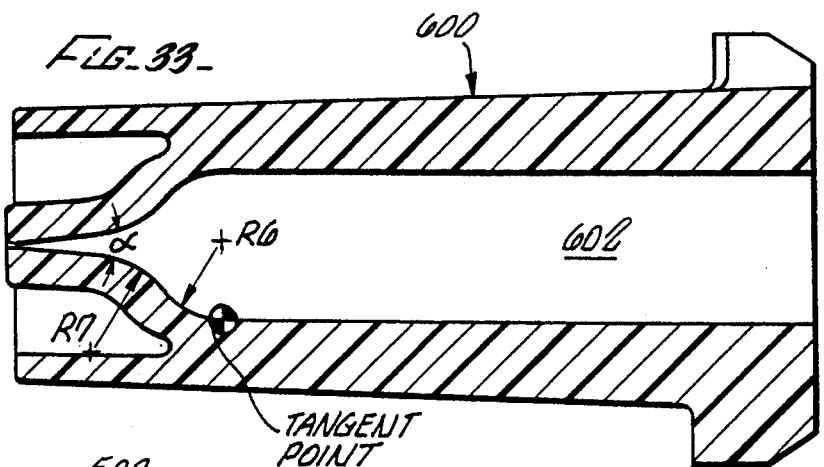
FIG. 33 is a section view of a fourth preferred ampule embodiment.

Ampule 500 carries 0.5 ml volume of injectant. Ampule 600 shown in FIG. 33 is similar to the ampule 500 but is formed with an injectant chamber 602 having a larger nominal injectant chamber diameter (0.304 in.) and holding 1.0 ml of injectant. Radii R6 and R7 are 0.22 in., alpha is 10 degrees, L is 0.021, the tangent point is 1.219 from the lug end, and the overal length is 1.647. The features shown on ampules 132 (FIG. 7) and 306 (FIG. 16), for example, the shield 160 or channels 336 for exhausting compressed gas may also be used with ampules 406 (FIG. 27), 500 (FIG. 30) or 600 (FIG. 33).

The nozzle section L/D ratio is another factor that helps maintain minimum jet spreading and transverse turbulent momentum. Ratios from 2 to 5 provide a good compromise to damp transverse velocity without incurring too high a nozzle pressure drop. An L/D ratio of 2.5 is most preferred. The nozzle diameter D ranges from approximately 0.0040 to 0.0250 in. With an L/D ratio of 2.5, L ranges from 0.0100 to 0.0625. The radius R5 in FIG. 32 is preferably 10×D.

P4 is preferably a sharp corner. A substantial radius at P4 will create a bell mouth design allowing the jet of injectant to possibly diverge as it exits the ampule during injection.

Figure 35:
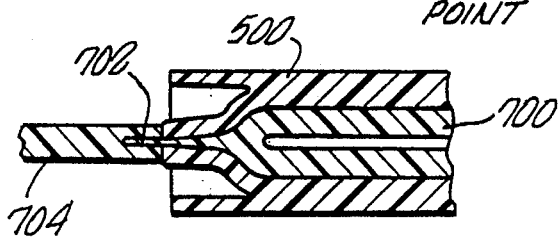
FIG. 35 is a section view fragment of tooling for molding ampule nozzles.

FIG. 35 shows manufacturing tooling for injection molding ampules, such as ampule 500. A core pin 700 has a fine wire tip 702 ground onto its leading end. The wire tip 702 extends into a matching hole in a pilot guide 704. The wire tip 702 allows for the injection molding of very small diameter orifice openings, facilitates sharp corners at P4 (FIG. 32), centers the nozzle opening and provides added rigidity to resist transverse flow of plastic during injection molding.

Thus, while several embodiments of the present invention have been shown and described, it will be obvious that many changes and modifications may be made thereunto, without departing from the spirit and scope of the invention.

We claim:

1. In an ampule of the type used with an injector to provide a needleless injection, and having an ampule body forming an injectant chamber and a nozzle section adjoining the ampule body and forming a nozzle opening, the improvement comprising:

a tubular shroud attached to the ampule body and concentric with the nozzle section; and a Luer fitting on the nozzle section and substantially within the shroud, the Luer fitting having a minimum diameter of approximately 0.15 inch adjacent to the nozzle opening and tapering linearly outwardly to larger diameters towards the injectant chamber.

2. The ampule of claim 1 wherein the injectant chamber is cylindrical and concentric with the nozzle opening.

3. The ampule of claim 1 further comprising means for attaching the ampule to an injection device.

4. The ampule of claim 3 wherein the means for attaching comprises a plurality of lug sections radially projecting from the ampule body and spaced apart from the nozzle section.

5. The ampule of claim 1 further comprising a plunger slidably positioned at least partially within the injectant chamber.

6. The ampule of claim 1 wherein the nozzle section projects beyond the tubular shroud.

7. The ampule of claim 1 further comprising:

a nozzle bore of length L in the nozzle section, a throat section between the ampule body and the nozzle section, the throat section having inner throat walls leading and tapering substantially conically outwardly from the nozzle bore towards the injectant chamber.

8. The ampule of claim 7 further comprising a transition section between, and adjoining, the throat section and the ampule body, the transition section having forward inner transition walls curving on a radius convexly from the throat section into rear inner transition walls, the rear inner transition walls curving on a radius concavely from the forward inner transition walls to the ampule body.

9. The ampule of claim 7 wherein the throat section has inner walls which flair conically outwardly from a center line of the ampule at an angle in the range of approximately 2°–6°.

10. The ampule of claim 7 wherein throat section has a length a plurality of times greater than the length of the nozzle bore L.

11. In an ampule of the type used with an injector to provide a needleless injection, and having an ampule body forming an injectant chamber and a nozzle section adjoining the ampule body and forming an nozzle opening, the improvement comprising:

a nozzle section having a nozzle bore of length L;

a throat section adjoining the nozzle section and having inner throat walls leading and tapering substantially conically outwardly from the nozzle bore, the throat section having a length a plurality of times greater than the length of the nozzle bore L;

a cylindrical ampule body adjoining the throat section and containing an injectant chamber;

a tubular shroud attached to the ampule body and extending substantially over the entire throat section; and a Luer fitting on the nozzle section substantially within the shroud.

12. The ampule of claim 11 wherein the shroud has a length of approximately 0.3 inches.

13. The ampule of claim 11 wherein the shroud has a forward end rim with an outside diameter of approximately 0.4 inch.

14. The ampule of claim 11 further comprising a plurality of lug sections radially projecting from the ampule body.

15. The ampule of claim 11 wherein the nozzle section projects beyond the tubular shroud.

16. The ampule of claim 11 further comprising a transition section between, and adjoining, the throat section and the ampule body, the transition section having forward inner transition walls curving on a radius convexly from the throat section into rear inner transition walls, the rear inner transition walls curving on a radius concavely from the forward inner transition walls to the ampule body.

17. The ampule of claim 11 wherein the throat section has inner walls which flair conically outwardly from a center line of the ampule at an angle in the range of approximately 2°–6°.

18. In an ampule of the type used with an injector to provide a needleless injection, and having an ampule body having a front and a back end and containing an injectant chamber and a nozzle section forming a nozzle and adjoining the ampule body, the improvement comprising:

a tubular shroud attached to the ampule body, concentric with the nozzle section;

a Luer fitting on the nozzle section and substantially within the shroud;

a conical throat section adjoining the ampule body and the nozzle section and forming a conical throat for connecting the injectant chamber to the nozzle; and a plurality of lugs at the back end of the ampule body radially spaced apart from each other.

* * * * *